United States Patent
Chavez et al.

(10) Patent No.: US 10,981,955 B2
(45) Date of Patent: Apr. 20, 2021

(54) METHOD OF MANUFACTURING A PHARMACEUTICAL COMPOSITION

(71) Applicant: FERRING B.V., Hoofddorp (NL)

(72) Inventors: Elizabeth Serrano Chavez, Copenhagen S (DK); Helen Sjoergren, Copenhagen S (DK); Jette Boll, Copenhagen S (DK); Hayley Reece, Nr. Penicuik (GB); Jonathan James Loughrey, Nr. Penicuik (GB)

(73) Assignee: FERRING B.V., Hoofddorp (NL)

( * ) Notice: Subject to any disclaimer, the term of this patent is extended or adjusted under 35 U.S.C. 154(b) by 0 days.

(21) Appl. No.: 16/637,499

(22) PCT Filed: Aug. 10, 2018

(86) PCT No.: PCT/EP2018/071832
§ 371 (c)(1),
(2) Date: Feb. 7, 2020

(87) PCT Pub. No.: WO2019/030412
PCT Pub. Date: Feb. 14, 2019

(65) Prior Publication Data
US 2020/0216500 A1 Jul. 9, 2020

(30) Foreign Application Priority Data

Aug. 11, 2017 (EP) .................... 17186048

(51) Int. Cl.
*C07K 7/16* (2006.01)

(52) U.S. Cl.
CPC ............ *C07K 7/16* (2013.01); *C07B 2200/13* (2013.01)

(58) Field of Classification Search
None
See application file for complete search history.

(56) References Cited

FOREIGN PATENT DOCUMENTS

WO   WO-2009/122285 A1   10/2009

OTHER PUBLICATIONS

Rudko et al., "Crystalline Salts of Oxytocin: X-Ray Crystallographic Data," Journal of Crystal Growth, vol. 10, No. 3, pp. 260-262 (Aug. 1971).

Byrn et al., "Pharmaceutical Solids: A Strategic Approach to Regulatory Considerations," Pharmaceutical Research, vol. 12, No. 7 (Jan. 1995).

*Primary Examiner* — Christina Bradley
(74) *Attorney, Agent, or Firm* — Foley & Lardner LLP

(57) ABSTRACT

The present invention relates to crystalline forms of carbetocin, a method of their manufacture, and pharmaceutical compositions thereof.

25 Claims, 11 Drawing Sheets

HPLC Chromatograms of Solids Isolated from Example 1

HPLC Chromatograms of Solids Isolated from Example 4

FIG. 6 HPLC Chromatograms of Solids Isolated in Example 5

DSC data for crystalline carbetocin isolated from Example 5

GVS change in mass plot for crystalline carbetocin isolated from Example 5

GVS isotherm plot for crystalline carbetocin isolated from Example 5

METHOD OF MANUFACTURING A PHARMACEUTICAL COMPOSITION

CROSS-REFERENCE TO RELATED APPLICATIONS

The present application is the U.S. National Stage of International Application No. PCT/EP2018/071832 filed Aug. 10, 2018, and claims priority to European Patent Application No. 17186048.9 filed Aug. 11, 2017.

The present invention relates to crystalline forms of carbetocin, a method of their manufacture, and pharmaceutical compositions thereof.

BACKGROUND

Carbetocin [(also known as 1-desamino-1-monocarba-2-(O-methyl)-tyrosine)oxytocin or 1-butanoic acid-2-(O-methyl-L-tyrosine)-1-carbaoxytocin] is a long-acting synthetic oligopeptide analogue of oxytocin, with agonist action. Carbetocin incorporates the following replacements relative to oxytocin: a) the amino-group of cysteine (position 1) by a hydrogen atom; b) of its disulphide bond by a thioether bond; and c) the hydroxyl group of tyrosine (position 2) by a methyloxyl group. Carbetocin (PABAL®, DURATOCIN®) is currently approved for the prevention of uterine atony following delivery of the infant by Caesarean section under epidural or spinal anaesthesia. The dosages used for this medical indication are relatively small, for instance of the order of 100 micrograms given once.

Recently, there has been an increased need for oxytocin receptor agonists, particularly carbetocin. For example, oxytocin receptors have recently been indicated in the treatment of Prader-Willi Syndrome (see WO2016/044131). Prader-Willi Syndrome is a genetic disorder characterised by hyperphagia, food seeking behaviour, rapid weight gain, compulsive behaviour and aggression in young children. As described in WO2016/044131, patients treated with carbetocin exhibit statistically significant improvement over placebo treated patients after 15 days in measurements of hyperphagia, obsessive compulsive disorder, food seeking behaviour and clinical global impression. A relatively large amount of peptide has to be produced for this indication, because the dosages used are significantly higher than those used in the treatment of uterine atony, for instance of the order of tens of milligrams per day, and the treatment is more long term. It would be desirable to produce relatively large amounts of carbetocin of high purity for such indications.

The synthesis of peptides may be carried out using solid phase synthetic procedures, which are well known in the art. Solution phase synthesis is an alternative method, which may be useful for small quantities of peptide. This stage of peptide production is known as the "upstream process", and results in the formation of a crude peptide product.

Following the synthesis of the crude peptide, it is usually necessary to separate the peptide of interest from various peptide and non-peptide impurities. This step is known as the purification step.

Many methods of purifying peptides are known in the art. However, peptide purification methods typically include at least one chromatographic step, for example size exclusion chromatography, hydrophobic interaction chromatography, ion exchange chromatography, free-flow-electrophoresis, affinity chromatography, high performance liquid chromatography (HPLC) etc. The most commonly employed form of HPLC is "reversed phase" HPLC (also known as RP-HPLC), in which peptides elute with increasing amounts of an organic solvent, such as acetonitrile, according to their hydrophobicity.

Following the purification step, the peptide typically has to be separated from volatile solvents. This step is known as the isolation step. Known methods of separating the peptide from the peptide from the solvents include ultrafiltration and lyophilisation.

Lyophilisation (also known as freeze-drying) comprises a step of rapid freezing of the peptide-containing solution, typically by immersing a container holding the solution in liquid nitrogen. The container is subsequently placed in a vacuum chamber, which comprises a cooling coil. The volatile solvents sublimate in the vacuum. The sublimation process ensures that the purified sample is kept cold.

Lyophilisation is the technique most commonly used in the art to isolate peptides from solution. This is principally because the technique is well known, reproducible and easy to carry out. Further, the stability of peptides is typically increased at low temperatures.

Methods for purification and isolation of carbetocin and related peptides are known in the art:

CN104592362 describes a step of liquid chromatography purification of carbetocin followed by lyophilisation. In most cases the liquid chromatography step is HPLC.

WO2015185584 describes the purification and lyophilisation of oxytocin agonists other than carbetocin.

CN102977192 describes a process of purifying carbetocin by combining liquid chromatography and ion exchange chromatography. After purification, the product goes through the step of desalination and lyophilisation.

CN104744567 describes a process of purifying carbetocin by ion exchange chromatography followed by lyophilisation.

CN101531705 describes a process of purifying carbetocin using reverse phase HPLC followed by transforming the product into an acetate salt using the ion exchange method. After being transformed into the salt, the product is subsequently lyophilised.

WO2009/122285 discloses a method of purifying oxytocin analogues involving an HPLC step followed by a step of lyophilisation. Rudko A D et al. "Crystalline Salts of Oxytocin: X-ray crystallographic data" *J. Crystal Growth*, vol. 10, no. 3, 1971, pages 260-262 describes the characterisation of crystallised oxytocin salts. Bryn S et al. "Pharmaceutical Solids: A Strategic Approach to Regulatory Considerations" *Pharmaceutical Research*, vol. 12, no. 7, 1995, pages 945-954 describes the characterisation of pharmaceutical solids.

It can be seen from the above references that there is a strong prejudice in the art towards using lyophilisation as the isolation step in the synthesis of carbetocin and other oxytocin receptor agonists.

However, there are several problems associated with lyophilisation, for example, a large amount of time has to be spent processing the peptide, and the cost of the refrigerant and equipment is very high.

These problems may be acceptable when producing a small amount of a peptide. However, when mass producing the peptide, lyophilisation becomes a "bottleneck" in the production process. Further, the proportion of the overall cost of production spent on lyophilisation increases with the mass of peptide produced.

Accordingly, there also exists a need in the art for an improved method of isolating. carbetocin to remove the lyophilisation "bottleneck" such that larger quantities of carbetocin of sufficient purity may be produced to meet the need in indications such as treatment of Prader-Willi Syndrome.

SUMMARY OF THE INVENTION

In one aspect, the present invention relates to carbetocin in crystalline form.

In a further aspect, the present invention relates to a method of manufacturing carbetocin in a crystalline form comprising the step of crystallising carbetocin.

In a further aspect, the present invention relates to a pharmaceutical composition comprising carbetocin according to the present invention, or carbetocin made according the present invention.

FIGURES RELATED TO THE PRESENT INVENTION

The drawings related to the present invention are described below:

DETAILED DESCRIPTION

Figure 1:
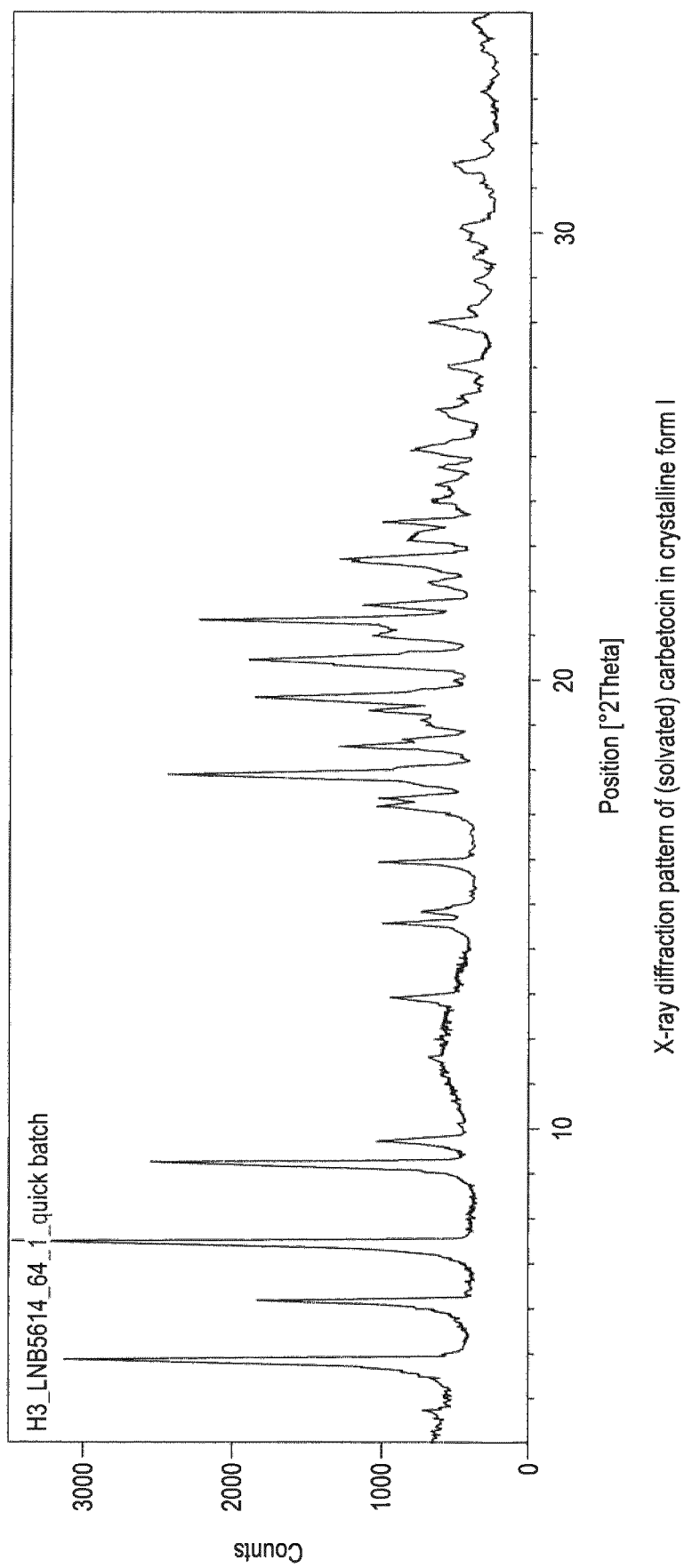
FIG. 1 shows the X-ray diffraction pattern (Cu) of solvated crystalline Form I carbetocin.

Carbetocin has not previously been known to form crystals. The present applicant surprisingly found that it was possible to form three crystalline forms of carbetocin, as described herein, two of which may be denoted Form I and Form II. Form I is solvated (for example hydrated), while Form II is desolvated. Form II has high stability (see FIG. 4B) and has an acceptably low ethylene glycol content (see Example 3), and may be used, for example, as a medicament. By acceptably low ethylene glycol content, it is meant an ethylene glycol content below the ICH limit of 620 ppm, as determined by gas chromatography. Form I may be used as a synthetic intermediate in the production of Form II. A third crystalline form is also described herein (see Example 5).

According to the present invention, from a first aspect, there is provided carbetocin in crystalline form. From a second aspect, there is provided carbetocin in a solvated (for example hydrated) crystalline form. From a third aspect, there is provided carbetocin in a desolvated crystalline form.

By solvated it is meant that the crystalline structure includes either ordered or disordered solvent molecules. By disordered it is meant that the positions of the solvent molecules or the positions of atoms therein may vary within the crystal structure. The solvent molecules may be liquid or gaseous at room temperature and atmospheric pressure. The solvent molecules may consist of molecules of only one type. Alternatively, the solvent molecules may consist of two or more different types of molecules (one of which may optionally be water). There may be at least 0.1 or more solvent molecules per molecule of carbetocin, for example at least 0.2 solvent molecules per molecule of carbetocin, for example at least 0.5 solvent molecules per molecule of carbetocin, for example at least 1 solvent molecule per molecule of carbetocin, for example at least 2 solvent molecules per molecule of carbetocin, for example at least 5 solvent molecules per molecule of carbetocin. As such, the carbetocin in a solvated crystalline form may be in the form of a mono-, di-, tri-, tetra-, penta-, or hexa-hydrate solvated crystalline form. Preferably, when the carbetocin is in solvated crystalline form, the solvated crystalline form is a monohydrate or a pentahydrate. Accordingly, in one aspect, carbetocin is in a monohydrate or pentahydrate crystalline form. Such carbetocin may include either ordered or disordered solvent molecules. It is believed that the number of solvent molecules does not affect whether they are ordered or disordered.

By desolvated it is meant that the crystalline structure includes little or no ordered or disordered solvent molecules. There may be less than or equal to 2 solvent molecules per molecule of carbetocin, for example less than or equal to 1 solvent molecule per molecule of carbetocin, for example less than or equal to 0.5 solvent molecules per molecule of carbetocin, for example less than or equal to 0.2 solvent molecules per molecule of carbetocin, for example less than or equal to 0.1 solvent molecules per molecule of carbetocin, for example less than or equal to 0.05 solvent molecules per molecule of carbetocin, for example less than or equal to 0.02 solvent molecules per molecule of carbetocin, for example less than or equal to 0.01 solvent molecules per molecule of carbetocin.

In order to determine the crystalline form, X-ray powder diffraction (XRPD) analysis can be carried out. In the present invention, XRPD analysis was carried out using Cu K radiation ($\alpha_1$ λ=1.54060 Å; $\alpha_2$=1.54443 Å; β=1.39225 Å; $\alpha_1$:$\alpha_2$ ratio=0.5) on a PANalytical X'pert pro, as further detailed in Example 1. The carbetocin in crystalline form and/or the carbetocin in a solvated crystalline form may be characterised by X-ray powder diffraction peaks at about 4.83, 7.43, 9.20, 17.87, 19.60, 20.43 and 21.34 degrees 2θ (Cu), and/or be characterised by an X-ray powder diffraction (Cu) pattern substantially as illustrated in FIG. 1, and/or characterised by having 5 or more, 6 or more, 7 or more, 8 or more, 9 or more, 10 or more, 11 or more, 12 or more, 13 or more, 14 or more, 15 or more, or substantially all of the (Cu) X-ray powder diffraction peaks as shown in Table 1. Accordingly, in one aspect, the carbetocin in crystalline form is characterised by X-ray powder diffraction peaks at about 4.83, 7.43, 9.20, 17.87, 19.60, 20.43, and 21.34 degrees 2θ carried out using Cu K radiation ($\alpha_1$ λ=1.54060 Å; $\alpha_2$=1.54443 Å; β=1.39225 Å; $\alpha_1$:$\alpha_2$ ratio=0.5).

Figure 2:
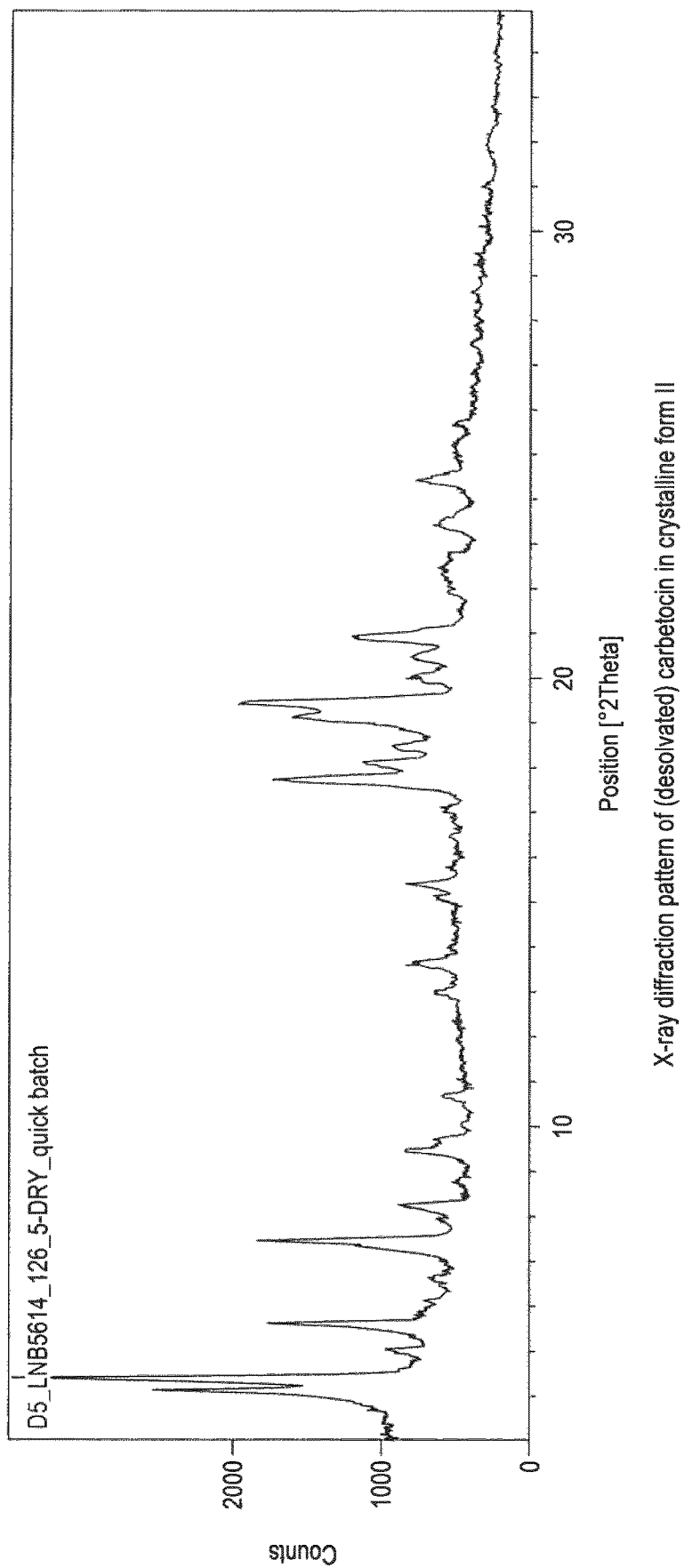
FIG. 2 shows the X-ray diffraction pattern (Cu) of desolvated crystalline Form II carbetocin.

The carbetocin in crystalline form and/or the carbetocin in an desolvated crystalline form may be characterised by X-ray powder diffraction peaks at about 4.11, 4.39, 5.60, 7.45, 17.75, 19.16 and 19.45 degrees 2θ (Cu) and/or be characterised by an X-ray powder diffraction (Cu) pattern substantially as illustrated in FIG. 2, and/or characterised by having 5 or more, 6 or more, 7 or more, 8 or more, 9 or more, 10 or more, 11 or more, 12 or more, 13 or more, 14 or more, 15 or more, or substantially all of the (Cu) X-ray powder diffraction peaks as shown in Table 2. Accordingly, in one aspect, the carbetocin in crystalline form is characterised by X-ray powder diffraction peaks at about 4.11, 4.39, 5.60, 7.45, 17.75, 19.16 and 19.454 degrees 2θ carried out using Cu K radiation ($\alpha_1$ λ=1.54060 Å; $\alpha_2$=1.54443 Å; β=1.39225 Å; $\alpha_1$:$\alpha_2$ ratio=0.5).

Figure 5:
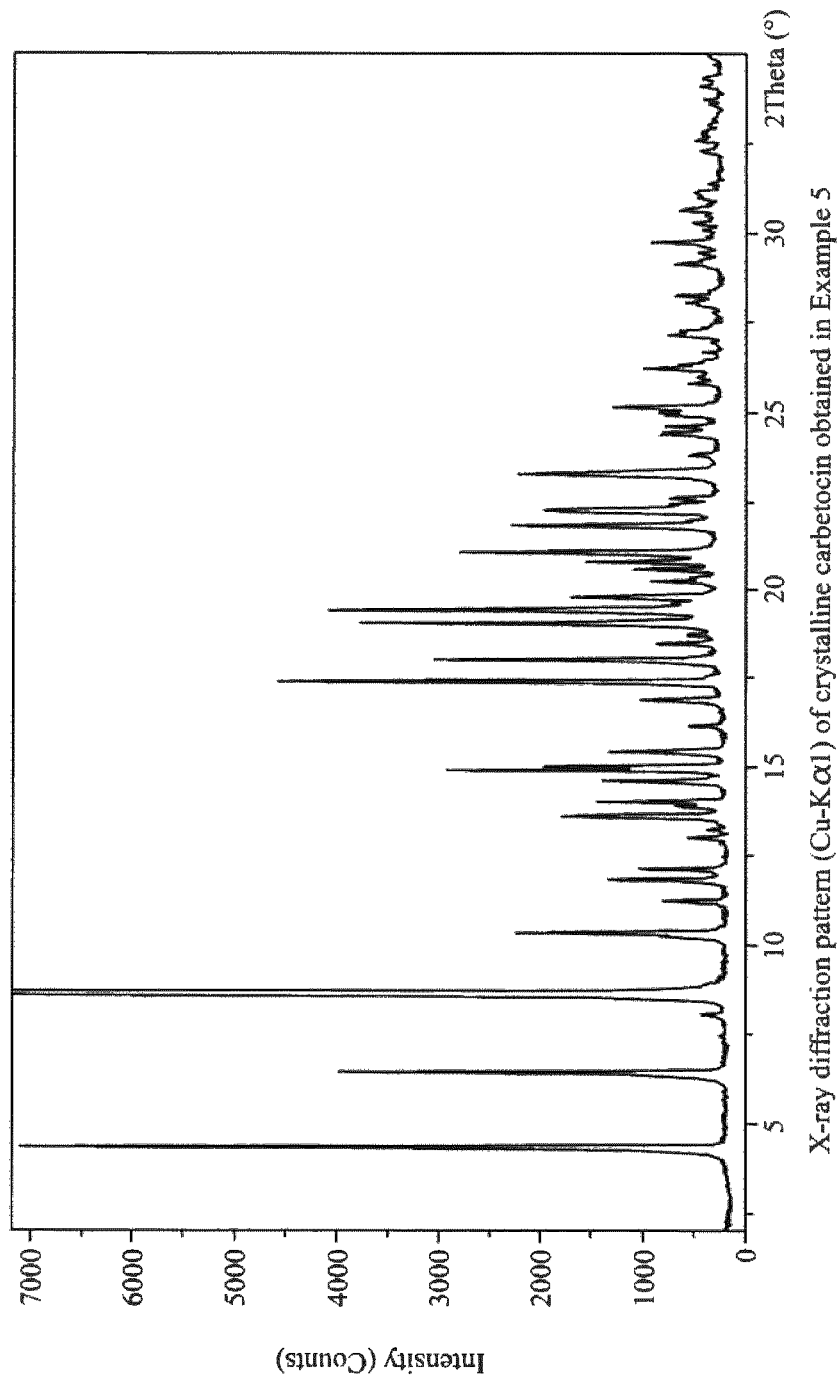
FIG. 5 shows the X-ray diffraction pattern (Cu—K$\alpha_1$) of crystalline carbetocin obtained in Example 5.
Figure 6:
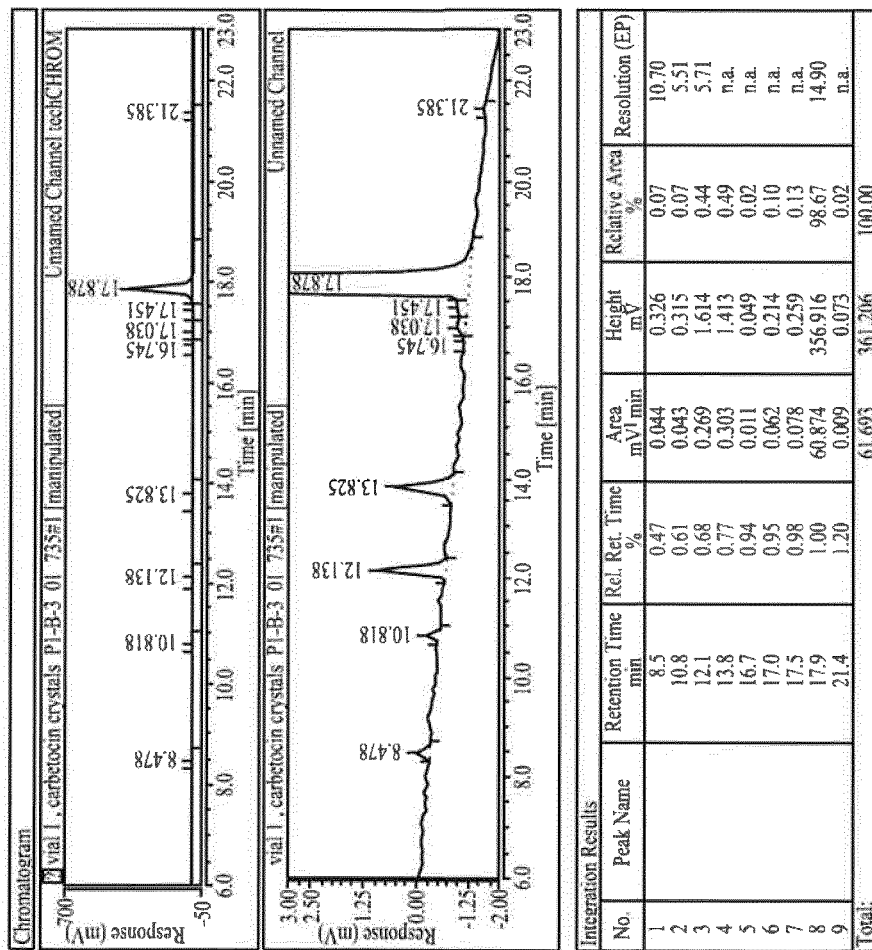
FIG. 6 shows the HPLC Chromatogram of Solids Isolated from Example 5.

The carbetocin in crystalline form may be characterised by X-ray powder diffraction peaks at about 4.34, 6.43, 8.66, 17.37, 19.03, and 19.39 degrees 2θ (Cu—K$\alpha_1$) and/or be characterised by an X-ray powder diffraction (Cu—K$\alpha_1$) pattern substantially as illustrated in FIG. 5, and/or characterised by having 5 or more, 6 or more, 7 or more, 8 or more, 9 or more, 10 or more, 11 or more, 12 or more, 13 or more, 14 or more, 15 or more, or substantially all of the (Cu—K$\alpha_1$) X-ray powder diffraction peaks as shown in Table 3. Accordingly, in one aspect, the carbetocin in crystalline form is characterised by X-ray powder diffraction peaks at about 4.34, 6.43, 8.66, 17.37, 19.03, and 19.39 degrees 2θ carried out using Cu K$\alpha_1$ radiation ($\alpha_1$ λ=1.54060 Å).

TABLE 1

(Cu—K) XRPD peak table for carbetocin in Form I. Bold highlighted peaks correspond to those being the highest peaks as identified in FIG. 1 (Examples 1 and 2).

| No. | Pos. [°2Th.] | FWHM [°2Th.] | Area [cts* °2Th.] | Backgr. [cts] | d-spacing [Å] | Height [cts] | Rel. Int. [%] |
|---|---|---|---|---|---|---|---|
| 1 | 3.65 | 0.15 | 12.77 | 532.33 | 24.19 | 84.36 | 2.65 |
| 2 | 4.83 | 0.06 | 171.97 | 431.53 | 18.30 | 2725.63 | 85.47 |
| 3 | 6.13 | 0.06 | 92.88 | 372.00 | 14.41 | 1472.12 | 46.16 |
| 4 | 7.43 | 0.06 | 201.21 | 347.68 | 11.90 | 3189.14 | 100.00 |
| 5 | 9.20 | 0.06 | 138.54 | 378.00 | 9.61 | 2195.83 | 68.85 |
| 6 | 9.69 | 0.05 | 31.51 | 393.01 | 9.13 | 624.18 | 19.57 |
| 7 | 11.54 | 0.15 | 35.71 | 427.00 | 7.67 | 235.80 | 7.39 |
| 8 | 12.88 | 0.08 | 39.37 | 421.00 | 6.87 | 519.95 | 16.30 |
| 9 | 14.56 | 0.08 | 46.76 | 384.19 | 6.08 | 617.61 | 19.37 |
| 10 | 14.82 | 0.09 | 31.97 | 378.00 | 5.98 | 361.95 | 11.35 |
| 11 | 15.91 | 0.06 | 41.67 | 361.00 | 5.57 | 660.49 | 20.71 |
| 12 | 17.17 | 0.08 | 51.12 | 380.00 | 5.16 | 675.24 | 21.17 |
| 13 | 17.35 | 0.08 | 49.08 | 384.00 | 5.11 | 648.19 | 20.33 |
| 14 | 17.87 | 0.09 | 182.84 | 392.21 | 4.96 | 2069.98 | 64.91 |
| 15 | 18.52 | 0.09 | 78.64 | 407.00 | 4.79 | 890.24 | 27.91 |
| 16 | 19.32 | 0.09 | 60.92 | 425.72 | 4.59 | 689.67 | 21.63 |
| 17 | 19.60 | 0.13 | 183.83 | 430.00 | 4.53 | 1456.81 | 45.68 |
| 18 | 20.43 | 0.08 | 110.35 | 436.00 | 4.35 | 1457.52 | 45.70 |
| 19 | 21.00 | 0.13 | 78.71 | 435.00 | 4.23 | 623.78 | 19.56 |
| 20 | 21.34 | 0.10 | 181.55 | 432.00 | 4.16 | 1798.48 | 56.39 |
| 21 | 21.68 | 0.10 | 70.60 | 429.00 | 4.10 | 699.32 | 21.93 |
| 22 | 22.18 | 0.13 | 34.30 | 427.00 | 4.01 | 271.82 | 8.52 |
| 23 | 22.69 | 0.08 | 67.05 | 428.00 | 3.92 | 885.61 | 27.77 |
| 24 | 23.16 | 0.13 | 49.67 | 426.00 | 3.84 | 393.60 | 12.34 |
| 25 | 23.53 | 0.08 | 43.92 | 422.00 | 3.78 | 580.07 | 18.19 |
| 26 | 24.00 | 0.08 | 18.57 | 415.00 | 3.71 | 245.25 | 7.69 |
| 27 | 24.38 | 0.10 | 24.25 | 407.00 | 3.65 | 240.19 | 7.53 |
| 28 | 24.77 | 0.10 | 22.01 | 397.82 | 3.59 | 218.03 | 6.84 |
| 29 | 25.16 | 0.18 | 73.75 | 385.57 | 3.54 | 417.45 | 13.09 |
| 30 | 26.01 | 0.26 | 61.97 | 356.00 | 3.43 | 245.56 | 7.70 |
| 31 | 26.33 | 0.10 | 15.08 | 344.00 | 3.39 | 149.38 | 4.68 |
| 32 | 27.02 | 0.15 | 39.17 | 314.12 | 3.30 | 258.68 | 8.11 |
| 33 | 28.00 | 0.10 | 42.85 | 289.00 | 3.19 | 424.44 | 13.31 |
| 34 | 28.95 | 0.15 | 15.10 | 287.00 | 3.08 | 99.73 | 3.13 |
| 35 | 29.47 | 0.10 | 12.50 | 282.00 | 3.03 | 123.80 | 3.88 |
| 36 | 30.14 | 0.13 | 27.59 | 272.00 | 2.97 | 218.68 | 6.86 |
| 37 | 31.53 | 0.15 | 44.27 | 255.00 | 2.84 | 292.33 | 9.17 |
| 38 | 32.07 | 0.15 | 14.80 | 249.00 | 2.79 | 97.75 | 3.07 |
| 39 | 33.16 | 0.15 | 15.43 | 238.00 | 2.70 | 101.91 | 3.20 |
| 40 | 34.17 | 0.20 | 16.62 | 260.00 | 2.62 | 82.33 | 2.58 |
| 41 | 34.74 | 0.18 | 26.54 | 275.00 | 2.58 | 150.26 | 4.71 |

TABLE 2

(Cu—K) XRPD peak table for carbetocin in Form II. Bold highlighted peaks correspond to those being the highest peaks as identified in FIG. 2 (Examples 3 and 4).

| No. | Pos. [°2Th.] | FWHM [°2Th.] | Area [cts* °2Th.] | Backgr. [cts] | d-spacing [Å] | Height [cts] | Rel. Int. [%] |
|---|---|---|---|---|---|---|---|
| 1 | 4.11 | 0.06 | 92.55 | 706.02 | 21.49 | 1466.93 | 64.40 |
| 2 | 4.39 | 0.06 | 143.71 | 676.49 | 20.14 | 2277.70 | 100.00 |
| 3 | 5.00 | 0.10 | 21.15 | 608.61 | 17.67 | 209.55 | 9.20 |
| 4 | 5.60 | 0.06 | 59.10 | 539.20 | 15.79 | 936.67 | 41.12 |
| 5 | 6.58 | 0.20 | 21.43 | 439.00 | 13.43 | 106.14 | 4.66 |
| 6 | 7.45 | 0.09 | 101.80 | 400.58 | 11.87 | 1152.49 | 50.60 |
| 7 | 8.22 | 0.08 | 25.45 | 359.83 | 10.75 | 336.08 | 14.76 |
| 8 | 9.45 | 0.10 | 36.87 | 343.00 | 9.36 | 365.24 | 16.04 |
| 9 | 10.67 | 0.10 | 15.60 | 344.00 | 8.29 | 154.56 | 6.79 |
| 10 | 12.99 | 0.15 | 22.36 | 397.00 | 6.82 | 147.70 | 6.48 |

TABLE 2-continued (Cu—K) XRPD peak table for carbetocin in Form II. Bold highlighted peaks correspond to those being the highest peaks as identified in FIG. 2 (Examples 3 and 4).

| No. | Pos. [°2Th.] | FWHM [°2Th.] | Area [cts* °2Th.] | Backgr. [cts] | d-spacing [Å] | Height [cts] | Rel. Int. [%] |
|---|---|---|---|---|---|---|---|
| 11 | 13.63 | 0.13 | 32.38 | 401.25 | 6.50 | 256.57 | 11.26 |
| 12 | 15.41 | 0.13 | 36.79 | 413.43 | 5.75 | 291.56 | 12.80 |
| 13 | 17.75 | 0.12 | 119.81 | 435.00 | 5.00 | 1054.98 | 46.32 |
| 14 | 18.12 | 0.12 | 54.63 | 437.00 | 4.90 | 481.03 | 21.12 |
| 15 | 18.48 | 0.15 | 54.81 | 438.00 | 4.80 | 361.98 | 15.89 |
| 16 | 19.16 | 0.15 | 141.75 | 435.00 | 4.63 | 936.10 | 41.10 |
| 17 | 19.45 | 0.12 | 139.15 | 433.00 | 4.56 | 1225.27 | 53.79 |
| 18 | 20.04 | 0.23 | 56.25 | 425.00 | 4.43 | 247.66 | 10.87 |
| 19 | 20.52 | 0.23 | 60.38 | 415.00 | 4.33 | 265.85 | 11.67 |
| 20 | 20.93 | 0.18 | 107.59 | 405.00 | 4.24 | 609.01 | 26.74 |
| 21 | 22.44 | 0.41 | 57.10 | 363.05 | 3.96 | 141.40 | 6.21 |
| 22 | 23.49 | 0.26 | 48.64 | 344.00 | 3.79 | 192.72 | 8.46 |
| 23 | 24.47 | 0.18 | 53.19 | 342.00 | 3.64 | 301.06 | 13.22 |
| 24 | 28.25 | 1.23 | 43.87 | 279.93 | 3.16 | 36.21 | 1.59 |
| 25 | 32.01 | 0.41 | 21.63 | 210.00 | 2.80 | 53.56 | 2.35 |

TABLE 3

(Cu-Kα1) XRPD peak table for carbetocin in crystalline form obtained as described in Example 5. The bold highlighted peaks correspond to those being the highest peaks identified in FIG. 5, Example 5.

| No. | Pos. [°2Th.] | d-spacing [Å] | Height [cts] | Rel. Int. [%] |
|---|---|---|---|---|
| 1 | 4.3370 | 20.25752 | 6599.52 | 14.31 |
| 2 | 6.4326 | 13.72947 | 3839.05 | 8.82 |
| 3 | 8.0491 | 10.97542 | 278.34 | 0.60 |
| 4 | 8.6648 | 10.19684 | 46121.51 | 100.0 |
| 5 | 10.2212 | 8.64745 | 643.40 | 1.40 |
| 6 | 10.3427 | 8.54606 | 1962.68 | 4.26 |
| 7 | 11.2271 | 7.87483 | 654.49 | 1.42 |
| 8 | 11.8251 | 7.47788 | 1174.88 | 2.55 |
| 9 | 12.1233 | 7.29461 | 856.51 | 1.86 |
| 10 | 13.0027 | 6.80318 | 394.87 | 0.86 |
| 11 | 13.2334 | 6.68508 | 226.41 | 0.49 |
| 12 | 13.6140 | 4.49901 | 1647.02 | 3.57 |
| 13 | 13.8708 | 6.37926 | 519.06 | 1.13 |
| 14 | 14.0103 | 6.31609 | 1269.77 | 2.75 |
| 15 | 14.5907 | 6.06611 | 1244.01 | 2.70 |
| 16 | 14.9012 | 5.94041 | 2710.87 | 5.88 |
| 17 | 15.0096 | 5.89774 | 1766.15 | 3.83 |
| 18 | 14.4094 | 5.74560 | 1182.73 | 2.56 |
| 19 | 16.1421 | 5.48642 | 413.17 | 0.90 |
| 20 | 16.8619 | 5.25382 | 858.21 | 1.86 |
| 21 | 17.3665 | 5.10226 | 4458.23 | 9.67 |
| 22 | 18.0048 | 4.92280 | 2842.92 | 6.16 |
| 23 | 18.4672 | 4.80057 | 720.50 | 1.56 |
| 24 | 18.7031 | 4.74055 | 404.75 | 0.88 |
| 25 | 19.0319 | 4.65939 | 3572.38 | 7.75 |
| 26 | 19.3918 | 4.57371 | 3844.17 | 8.33 |
| 27 | 19.7778 | 4.48530 | 1577.37 | 3.42 |
| 28 | 20.2075 | 4.39089 | 774.88 | 1.68 |
| 29 | 20.5431 | 4.31990 | 925.40 | 2.01 |
| 30 | 20.7560 | 4.27609 | 1394.51 | 3.02 |
| 31 | 21.0184 | 4.22328 | 2728.11 | 5.92 |
| 32 | 21.7698 | 4.07918 | 2143.36 | 4.65 |
| 33 | 22.1539 | 4.00932 | 1416.60 | 3.07 |
| 34 | 22.5554 | 3.93886 | 605.37 | 1.31 |
| 35 | 23.2290 | 3.82613 | 2097.57 | 4.55 |
| 36 | 23.7449 | 3.74416 | 396.84 | 0.86 |
| 37 | 24.3125 | 3.65802 | 690.11 | 1.50 |
| 38 | 24.5465 | 3.62368 | 629.24 | 1.36 |
| 39 | 24.8555 | 3.57932 | 578.44 | 1.25 |
| 40 | 25.0834 | 3.54732 | 1119.99 | 2.43 |
| 41 | 25.7775 | 3.45335 | 406.85 | 0.88 |
| 42 | 26.1605 | 3.40365 | 804.34 | 1.74 |
| 43 | 26.6344 | 3.34416 | 270.06 | 0.59 |
| 44 | 27.1068 | 3.28694 | 596.21 | 1.29 |
| 45 | 28.0519 | 3.17831 | 434.48 | 0.94 |
| 46 | 28.2113 | 3.16072 | 543.61 | 1.18 |
| 47 | 29.1046 | 3.06570 | 533.43 | 1.16 |
| 48 | 29.4103 | 3.03452 | 272.68 | 0.59 |
| 49 | 29.7218 | 3.00343 | 765.65 | 1.66 |
| 50 | 30.0597 | 2.97044 | 271.38 | 0.59 |

Table 3 shows the data obtained from Example 5. It will be noted that the radiation source for the values as reported in Table 3 is a Cu—Kα$_1$ source, whereas the radiation source for the values as reported in Tables 1 and 2 is a Cu—K source. The above XPRD peak table, Table 3 (FIG. 5, Example 5), nevertheless indicates carbetocin of a different crystal form or polymorph when compared to Examples 1 and 2 (FIG. 1, Table 1) and Examples 3 and 4 (FIG. 2, Table 2).

According to the present invention in a further aspect, there is provided a method of manufacturing carbetocin in a crystalline form, the method comprising a step of crystallising carbetocin.

By crystallising it is meant the process of forming a crystalline form of carbetocin from carbetocin dissolved in a solvent. By crystalline form is meant a solid material with a regularly repeating internal arrangement of atoms and external plane faces. Crystalline forms may be distinguished from amorphous forms on the basis of X-ray powder diffraction analysis. Crystalline forms are characterised by X-ray powder diffraction peaks as described herein. In amorphous solid forms the XPRD pattern is essentially continuous in appearance, i.e. without distinct peaks.

The carbetocin in a crystalline form may be crystallised from a mixture comprising carbetocin and one or more liquid(s), the one or more liquid(s) optionally comprising one or more liquid(s) from the group consisting of water, aqueous acetate buffer, ethylene glycol, acetonitrile, ethanol, methanol, propanol, isopropanol, 1,2-propanediol and dimethylformamide, for example a mixture of ethylene glycol and acetonitrile, for example a mixture of ethanol, ethylene glycol and acetonitrile, for example a mixture of propanol, ethylene glycol and acetone, for example a mixture of isopropanol, ethylene glycol and acetone, for example a mixture of dimethylformamide, ethylene glycol and acetonitrile, for example a mixture of dimethylformamide and acetonitrile, for example a mixture of dimethylformamide and acetone, for example a mixture of ethanol and acetonitrile, for example a mixture of methanol and acetonitrile, for example a mixture of 1,2-propanediol and acetonitrile, for example a mixture of 1,2-propanediol and acetone. Where the one or more liquids comprises two or more liquids, one of the liquids of the two or more liquids may be an antisolvent (as defined below). The one or more liquid(s) may comprise ethylene glycol and antisolvent in a ratio of from 15:85 to 25:75, for example a ratio of from 17.5:82.5 to 22.5:77.5, for example a ratio of about 20:80, and wherein the addition of antisolvent alters the ratio of ethylene glycol to acetonitrile to a ratio of from 1:99 to 30:70, for example a ratio of from 2:98 to 25:75, for example a ratio of from 3:97 to 20:80, for example a ratio of from 5:95 to 20:80, for example a ratio of from 5:95 to 15:85, for example a ratio of from 7.5:92.5 to 12.5:87.5, for example a ratio of about 10:90, for example a ratio of from 5:95 to 10:90, for example a ratio of 5:95 to 7.5:92.5, for example a ratio of about 6.7:93.3.

The one or more liquid(s) may comprise a mixture of ethylene glycol and acetonitrile.

The one or more liquid(s) may comprise ethylene glycol and acetonitrile in a ratio of from 1:99 to 50:50, for example a ratio of from 2:98 to 40:60, for example a ratio of from 3:97 to 35:65, for example a ratio of from 5:95 to 35:65, for example a ratio of from 8:92 to 30:70, for example a ratio of from 10:90 to 30:70, for example a ratio of from 15:85 to 25:75, for example a ratio of from 17.5:82.5 to 22.5:77.5, for example a ratio of about 20:80.

The one or more liquid(s) may comprise water. The one or more liquid(s) may comprise aqueous acetate buffer. In a particular aspect, the carbetocin in crystalline form is crystallised from a mixture comprising carbetocin and one or more liquid(s), the one or more liquid(s) comprising one or both of water and aqueous acetate buffer.

In one embodiment, the one or more liquid(s) may be water. If the one or more liquid(s) is water, the water may have a pH of between about 2 and 6, preferably a pH between about 3 and 4, more preferably a pH of about 3.5.

In one embodiment, the one or more liquid(s) may be aqueous acetate buffer. The aqueous acetate buffer may be formed from an aqueous mixture of acetic acid and an acetate salt. The acetate salt may be any salt of acetate with a suitable counterion. A suitable counterion may be, for instance, an alkali metal ion, an alkaline earth metal ion or an organic cation. The counterion may be lithium, sodium, potassium, magnesium, calcium or ammonium. Preferably, the counterion may be sodium or potassium, most preferably, the counterion may be sodium. Preferably, the aqueous acetate buffer has a pH of between about 4 and 7, preferably a pH between about 5 and 6, most preferably the pH is about 5.5. Preferably, the aqueous acetate buffer has a concentration of between 20 and 30 mM, most preferably the concentration is about 25 mM.

The carbetocin in crystalline form may be obtained by cooling the mixture comprising carbetocin and the one or more liquid(s), for example from 40° C. to 5° C., or by cycling the temperature of the mixture comprising carbetocin and one or more liquid(s), for example between 40° C. and 5° C. The temperature may be changed at a rate of 5° C. to 50° C. per hour, such as 35° C. per hour. By cycling the temperature of the mixture it is meant that the temperature must be subsequently lowered then raised, or vice versa. The temperature may be lowered then raised, or vice versa, two or more times, for example three or more times, for example four or more times, for example five or more times, for example ten or more times. Following cooling or cycling of the temperature of the mixture comprising carbetocin and one or more liquids, the temperature may be maintained, such as at 5° C., for a suitable length of time to form crystalline carbetocin. Typically, crystalline carbetocin may form and may be isolated within 6 hours to 24 hours, such as at about 12 hours or at about 18 hours. The cooling, cycling or maintenance of the temperature may occur with or without agitation of the mixture.

Alternatively, the carbetocin in crystalline form may unexpectedly be obtained by maintaining a mixture comprising carbetocin and water, or a mixture comprising carbetocin and aqueous acetate buffer, at a temperature of at least 15° C., such as 20° C., such as 30° C., such as 40° C. for a suitable length of time to form crystalline carbetocin. Typically, crystalline carbetocin forms between 3 to 100 days, more typically between 3 to 60 days, most typically between 7 to 12 days. In one alternative embodiment, the carbetocin in crystalline form may be obtained by maintaining a mixture comprising carbetocin and water, or a mixture comprising carbetocin and aqueous acetate buffer, at a temperature of 20° C., for about 3 to 60 days. In another alternative embodiment, the carbetocin in crystalline form may be obtained by maintaining a mixture comprising carbetocin and water, or a mixture comprising carbetocin and aqueous acetate buffer, at a temperature of 40° C. for about 7 to 12 days. In these alternative embodiments, all other steps described below, with the exception of the step related to addition of an antisolvent, may be performed.

The carbetocin may be crystallised from a mixture containing at least one solvent and at least one antisolvent. By solvent is meant a liquid in which carbetocin is readily dissolves or is readily soluble. The solvent may be any solvent in which carbetocin is soluble in an amount at is soluble in an amount at standard conditions of 0.01 mg/ml or greater, for example 0.05 mg/ml or greater, for example 0.1 mg/ml or greater, for example 0.5 mg/ml or greater, for example 1 mg/ml or greater, for example 5 mg/ml or greater, for example 10 mg/ml or greater, for example 20 mg/ml or greater. By antisolvent is meant a liquid in which carbetocin dissolves less readily relative to a solvent, or in which carbetocin is, relatively to a solvent, less soluble. The antisolvent may be selected relatively to the solvent and may be any solvent in which carbetocin is soluble in an amount at standard conditions of less than 20 mg/ml, for example less than 10 mg/ml, for example less than 5 mg/ml, for example less than 1 mg/ml, for example less than 0.5 mg/ml, for example less than 0.1 mg/ml, for example less than 0.05 mg/ml, for example less than 0.01 mg/ml. It will be understood by the skilled person that when carbetocin is soluble in an amount of, for example, 10 mg/ml or greater in a solvent, in an antisolvent it will be less soluble, i.e. it will be soluble in an amount of less than 10 mg/ml, for example less than 5 mg/ml, for example less than 1 mg/ml, for example less than 0.5 mg/ml, for example less than 0.1 mg/ml, for example less than 0.05 mg/ml, for example less than 0.01 mg/ml. Unless otherwise specified, the terms solvent and antisolvent refer to the solubility behaviour of carbetocin at room temperature and atmospheric pressure.

The solvent may comprise one or more liquid(s) from the group consisting of water, aqueous acetate buffer, ethylene glycol, ethanol, methanol, propanol, isopropanol, and 1,2-propanediol, The solvent may have a relative polarity index (RPI), as described by Christian Reichardt (*Solvents and Solvent Effects in Organic Chemistry*, Wiley-VCH Publishers, $3^{rd}$ ed., 2003) of greater than 0.5, for example greater than 0.6, for example greater than 0.7, for example greater than 0.8, for example greater than 0.9, for example greater than 1.0. The solvent may be or comprise any one or more of water, an aqueous acetate buffer solution, or an alcohol, for example any one or more of, water (RPI=1.000), an aqueous acetate buffer solution, ethylene glycol (RPI=0.790). ethanol (RPI=0.654), methanol (RPI=0.762), propanol (RPI=0.803), isopropanol (RPI=0.787), or 1,2-propanediol (RPI=0.72).

The carbetocin in a crystalline form may be crystallised from a mixture comprising carbetocin and one or more liquid(s), the carbetocin being present in a solvent at a concentration of from about 1 mg/ml to 200 mg/ml, preferably from about 10 mg/ml to 150 mg/ml, most preferably from about 20 mg/ml to 100 mg/ml. In one embodiment, the solvent may be water. In one embodiment, the solvent may be aqueous acetate buffer. In one embodiment, the solvent may be ethylene glycol.

The method may comprise a further step of adding an antisolvent to the mixture comprising carbetocin and one or more liquid(s), for example adding the antisolvent prior to cooling the mixture.

The antisolvent may have a relative polarity index (RPI), as described by Christian Reichardt (*Solvents and Solvent Effects in Organic Chemistry*, Wiley-VCH Publishers, 3$^{rd}$ ed., 2003) of less than 1, for example less than 0.9, for example less than 0.8, for example less than 0.75, for example less than 0.7, for example less than 0.6, for example less than 0.5. The antisolvent may be or comprise any one or more of, an ester, a ketone, a nitrile, or an ether, for example any one or more of, acetonitrile (RPI=0.460), ethyl acetate (RPI=0.228), acetone (RPI=0.355), or methyl tert-butyl ether (RPI=0.124).

Thus, in one embodiment of the method, carbetocin may be crystallised from a mixture comprising carbetocin and one or more liquid(s), the one or more liquid(s) comprising ethylene glycol and acetonitrile. The carbetocin may be present in the mixture comprising carbetocin and one or more liquid(s) at a concentration of from 10 mg/ml to 150 mg/ml, most preferably at about 100 mg/ml. The ethylene glycol and acetonitrile may be present in a ratio of from 5:95 to 35:65. The carbetocin in crystalline form may be obtained by cooling the mixture comprising carbetocin and the one or more liquid(s) from 40° C. to 5° C. at a rate of 35° C. per hour and maintaining the temperature at 5° C. for a suitable length of time to form crystalline carbetocin, such as for about 12 hours or for about 18 hours.

The method may comprise a further step of seeding the mixture comprising carbetocin and one or more liquid(s) with a crystal, for example a carbetocin crystal, for example a crystal of the solvated crystalline Form I of carbetocin.

By seeding is meant adding homogeneous or heterogeneous crystals, i.e. seed crystals, to the mixture to nucleate and/or grow additional carbetocin in a crystalline form. By homogeneous crystals is meant crystalline carbetocin in either of its forms. By heterogeneous crystals is meant crystals of another material.

The method may comprise a further step of inducing crystallisation in the mixture comprising carbetocin and one or more liquid(s). Crystallisation may be induced by any suitable means to promote nucleation and growth of crystals, for example by disturbing the surface of the mixture comprising carbetocin and one or more liquid(s) to create seed crystals, such as by pipetting liquid up and down from the surface of the mixture comprising carbetocin and one or more liquid(s) or scratching where the surface of the mixture comprising carbetocin and one or more liquid(s) meets the surface of the container in which the mixture is held.

The method may comprise a further step of desolvating and optionally drying the carbetocin in a crystalline form.

By desolvating is meant removal of some or substantially all of the solvated molecules from the crystalline structure of carbetocin, such that the crystalline structure includes little or no ordered or disordered solvent molecules. In a preferred embodiment, desolvating means converting carbetocin from a pentahydrate crystalline form to a monohydrate crystalline form.

The desolvation of the carbetocin in a crystalline form may be carried out by washing the carbetocin in a crystalline form in an antisolvent, for example acetonitrile, optionally at a temperature at or below 20° C., for example from −30° C. to 20° C., for example from −20° C. to 20° C., for example from −10° C. to 20° C., for example from −5° C. to 15° C., for example from 0° C. to 10° C., for example about 5° C., and then drying, for example drying under vacuum. The drying may occur under vacuum for a suitable length of time to effect the desolvation, such as for greater than 1 hour, such as for about 24 hours. Preferably, the carbetocin in a crystalline form may be washed in acetonitrile at a temperature of about 5° C. and dried under vacuum at a temperature of about 20° C. for about 24 hours to effect desolvation.

Desolvation may also be carried out by heating the carbetocin in a crystalline form to a temperature of at least 40° C. to at most 190° C., or by exposing carbetocin in a crystalline form to an environment of low relative humidity, such as 40% relative humidity or less.

Thus, in one embodiment of the method, carbetocin may be crystallised from a mixture comprising carbetocin and one or more liquid(s), the one or more liquid(s) comprising ethylene glycol and acetonitrile. The carbetocin may be present in the mixture comprising carbetocin and one or more liquid(s) at a concentration of from 10 mg/ml to 150 mg/ml, most preferably at about 100 mg/ml. The ethylene glycol and acetonitrile may be present in a ratio of from 5:95 to 35:65. Additional antisolvent, such as acetonitrile, may be added. The carbetocin in crystalline form may be obtained by cooling the mixture comprising carbetocin and the one or more liquid(s) from 40° C. to 5° C. at a rate of 35° C. per hour and maintaining the temperature at 5° C. for a suitable length of time to isolate crystalline carbetocin, such as for about 12 hours or for about 18 hours. The carbetocin in a crystalline form may be washed in acetonitrile at a temperature of about 5° C. and dried under vacuum at a temperature of about 20° C. for about 24 hours to effect the desolvation.

Optionally, a filtration step can be carried out prior to crystallisation. The filtration step preferably comprises filtration by centrifugation. Accordingly, in one aspect, the method of manufacturing carbetocin in a crystalline form comprises the steps of (1) filtration, preferably by centrifugation; and (2) crystallisation.

Optionally, a washing step can be carried out prior to crystallisation. For example, the carbetocin, for example crude carbetocin, may be slurried, for example slurried in acetonitrile, for example slurried in acetonitrile for 2 hours to a week, for example slurried in acetonitrile for about 18 hours with constant agitation. Washing crude carbetocin increases the purity prior to crystallisation by approximately 1 to 2% and significantly increases the assay values from around 44% to around 70% (in acetonitrile). Accordingly, in one aspect, the method of manufacturing carbetocin in a crystalline from comprises the steps of (1) washing carbetocin, for example crude carbetocin, in acetonitrile; and (2) crystallisation. In another aspect, the method of manufacturing carbetocin in crystalline form comprises the steps of (1) washing carbetocin, for example crude carbetocin, in acetonitrile; (2) filtration, preferably by centrifugation; and (3) crystallisation.

The applicants have advantageously and surprisingly found that it is possible to isolate carbetocin without any requirement for lyophilisation by crystallising the carbetocin, for example crystallising the carbetocin from solution.

The method provides high purity carbetocin in an acceptable yield without the need for a lyophilisation step.

The carbetocin in the mixture comprising carbetocin and one or more liquid may be substantially pure carbetocin, or alternatively may be crude carbetocin.

Herein, the term "crude" as in, "crude carbetocin" means carbetocin which is insufficiently pure to be used as a pharmaceutical product. The crude peptide may have a purity of less than 95%, for example less than 92.5%, for example from 90% to 93%, for example from 91% to 93%, as measured by UV-HPLC. The impurities found in the crude peptide may include one or more of inorganics, residual solvent (for example DMF), peptide-related impurities and residual peptide coupling reagents.

The (product) carbetocin in crystalline form/carbetocin in solvated (for example hydrated) crystalline form/carbetocin in desolvated crystalline form may have purity greater than or equal to 95%.

The crude carbetocin may be synthesised by methods well known in the art, for example the methods analogous to those described in WO2009/122285 (International Patent Application No. PCT/IB2009/005351) of Ferring B.V.

According to the invention in a further aspect there is provided a pharmaceutical composition including carbetocin according to the invention, or carbetocin made according to a method of the invention. The pharmaceutical composition of the invention may be for use as a medicament. The pharmaceutical composition of the invention may be for use in the treatment of a neurological disorder or reproductive disorder, for example for use in the treatment of Prader-Willi syndrome (as described in WO2016/044131 (International Patent Application No. PCT/US2015/04911) of Ferring B.V.); or for example for use in the treatment or prevention of uterine atony, for example following vaginal delivery of the infant, delivery of the infant by Caesarean section; or for use in the treatment or prevention of uterine atony in a patient who is at risk of developing postpartum hemorrhage (PPH); and/or for use in the treatment or prevention of excessive bleeding following vaginal delivery (as described in WO2009/122285 (International Patent Application No. PCT/IB2009/005351) of Ferring B.V).

The present invention is exemplified below. The examples may describe preferred embodiments of the invention but are not meant to be limiting in any way.

Example 1—Preparation of Solvated Crystalline Form I Carbetocin

Step i: Synthesis

Crude carbetocin of purity approx. 91% was obtained by synthetic methods analogous to those described in WO2009/122285 (International Patent Application No. PCT/IB2009/005351) of Ferring B.V.

Step ii: Preparation of the Solution 60 mg crude carbetocin obtained in step i) was dissolved in 0.6 mL of a 30:70 (v/v) mixture of ethylene glycol (first liquid): acetonitrile (second liquid) at 40° C. The vessel was then seeded with Form I (solvated) carbetocin crystals. It will be appreciated that seeding is not required, but may expedite the crystallisation.

Step iii: Crystallisation

The solution obtained in step ii) was heated to 40° C. and kept at this temperature for 30 minutes. The mixture was then filtered by centrifugation to remove any insoluble impurities. The mixture was then stirred at 40° C. for thirty minutes, cooled to 5° C. over the course of one hour, and then held at 5° C. for overnight with constant agitation.

The precipitated material was isolated.

XRPD analysis was carried out on a PANalytical X'pert pro. The samples were scanned between 3 and 35° 2θ. The material was gently ground to release any agglomerates and loaded onto a multi-well plate with Kapton or Mylar polymer film to support the sample. The multi-well plate was then placed into the diffractometer and analysed using Cu K radiation ($\alpha_1$ λ=1.54060 Å; $\alpha_2$=1.54443 Å; β=1.39225 Å; $\alpha_1:\alpha_2$ ratio=0.5) running in transmission mode (step size 0.0130° 2θ) using 40 kV/40 mA generator settings.

Carbetocin having a X-ray diffraction pattern substantially as shown in Table 1 and FIG. 1 (Form I) crystallised from the solution.

Figure 4A:
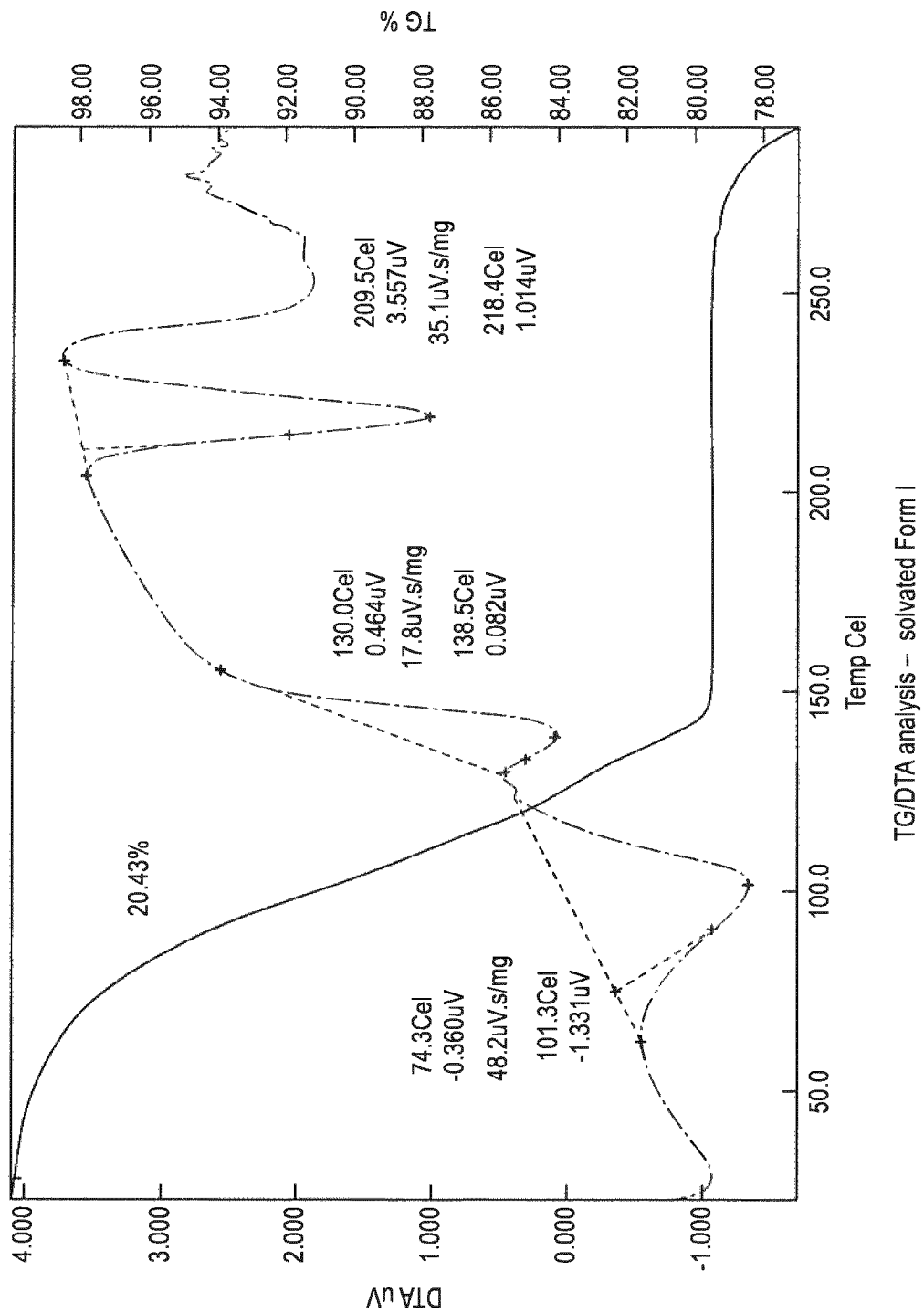
FIG. 4 shows TG/DTA data relating to solvated crystalline Form I carbetocin from Example 1 (FIG. 4a) and desolvated crystalline form II carbetocin from Example 4 (FIG. 4b).

The solids were analysed by TG/DTA for ease of mass loss/thermal events (FIG. 4a).

Figure 3A:
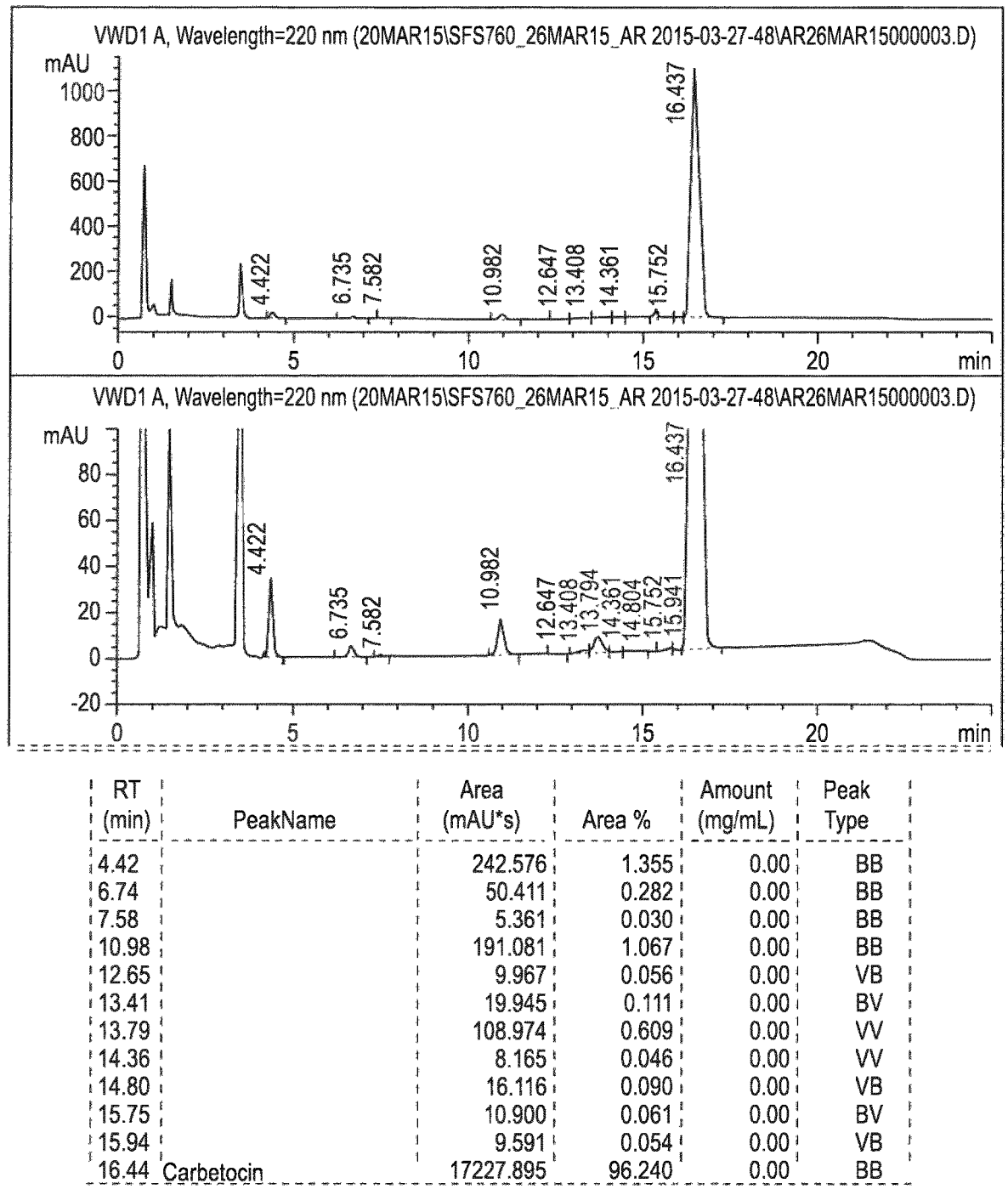
FIG. 3 shows HPLC Chromatograms of Solids Isolated from Example 1 (FIG. 3a); and Solids Isolated from Example 4 (FIG. 3b).

The purity of the carbetocin in the (solvated) crystalline form was calculated at 96.2% by UV-HPLC (FIG. 3a) according to the method outlined in Table 4.

TABLE 4

| Analytical HPLC parameters for Example 1 | | | |
|---|---|---|---|
| Parameter | Setting | | |
| LC | HPLC including: Gradient pump UV detector Autosampler Column heater (60° C.) | | |
| Column | Waters XBridge C18, 150 × 2.1 mm, 3.5 μm | | |
| Mobile phase A | ammonium acetate 0.30 g/L in water | | |
| Mobile phase B | 50% Mobile Phase A: 50% Acetonitrile (% v/v) | | |
| Flow rate | 0.8 mL/min | | |
| Injection volume | 40 μL | | |
| Detection | UV 220 nm | | |
| Column temperature | 60° C. | | |
| Autosampler temperature | 5° C. | | |
| Gradient | Time (min.) | % A | % B |
| | 0 | 100 | 0 |
| | 20 | 75 | 25 |
| | 21 | 100 | 0 |
| | 25 | 100 | 0 |
| Sample preparation | Crystals dissolved in milli-Q water and diluted to approx. 0.5 mg/mL with milli-Q water | | |
| Evaluation of results | Purity determined as relative UV area % of total area. | | |

Example 2—Preparation of Solvated Crystalline Form I Carbetocin

Step i: Synthesis

Crude carbetocin of purity approx. 91% was obtained by synthetic methods analogous to those described in WO2009/122285 (International Patent Application No. PCT/IB2009/005351) of Ferring B.V.

Step ii: Preparation of the Solution 60 mg crude carbetocin obtained in step i) was dissolved in 0.6 mL of a 30:70 (v/v) mixture of ethylene glycol (first liquid):acetonitrile (second liquid) at 40° C. The vessel was then seeded with Form 1 (solvated) carbetocin crystals. It will be appreciated that seeding is not required, but may expedite the crystallisation.

Step iii: Addition of Antisolvent

Sufficient Acetonitrile was added to adjust the ratio of ethylene glycol:acetonitrile to 6.7:93.3 (v/v)

Step iv: Crystallisation

The solution obtained in step iii) was heated to 40° C. and kept at this temperature for 30 minutes. The mixture was then filtered by centrifugation to remove any insoluble impurities. The mixture was then stirred at 40° C. for thirty minutes, cooled to 5° C. over the course of one hour, and then held at 5° C. overnight with constant agitation.

The precipitated material was isolated.

XRPD analysis was carried out as described above with respect to Example 1.

Carbetocin having a X-ray diffraction pattern substantially as shown in Table 1 and FIG. 1 crystallised from the solution.

Example 3—Preparation of Desolvated Crystalline Form II Carbetocin

In order to remove ethylene glycol present in the crystallised material produced by Examples 1 and 2, the crystallised material of Example 1 or Example 2 was desolvated and dried.

Washing the crystallised Form I material in acetonitrile at 5° C. followed by drying under vacuum resulted in the desolvation of solvated Form I, to produce desolvated Form II crystals, which have a diffraction pattern substantially as shown in Table 2 and FIG. 2. The Form II crystals were found to have ethylene glycol levels below the ICH limit of 620 ppm as determined by gas chromatography, with parameters as in Table 5 below.

TABLE 5

Gas chromatography parameters
Column: Agilent J&W D-B-624, 30 m × 0.32 mm, 1.8 μm d.f.

| | |
|---|---|
| Oven Temperature: | Initial: 35° C. (hold 1 min) |
| | Ramp: 6° C./min to 60° C. (hold 0 min) |
| | Ramp: 12° C./min to 225° C. (hold 0 min) |
| Injector Temperature | 230° C. |
| Injection Pressure | 3.7 psi |
| Injection Mode | Split |
| Injection Split ratio; Split flow; Total Flow | 10:1; 15.0 mL/min; 22.7 mL/min |
| Injection volume | 1 μL |
| Detector Temperature | 250° C. |
| Detector Hydrogen | 30.0 mL/min |
| Detector Air | 330 mL/min |
| Make-up Flow | 10.0 mL/min |
| Make-up Gas | Air |

Example 4—Preparation of Desolvated Crystalline Form II Carbetocin

To approximately 300 mg of crude carbetocin (purity approximately 91.3%), 3 ml of a pre-prepared 30% ethylene glycol: 70% acetonitrile (v/v) solvent mixture was added and the mixture heated to 40° C. for 30 minutes with constant agitation.

After 30 minutes, the mixture was filtered by centrifugation to remove any insoluble impurities. To this mixture (still at 40° C.), 1.5 ml acetonitrile was added in 0.5 ml aliquots. No precipitation was observed at 40° C., even after the complete addition of the acetonitrile.

The mixture was then stirred at 40° C. for 1 hour, and cooled to 5° C. over the course of 1 hour and then held at 5° C. for 18 hours with constant agitation.

After 18 hours, precipitated material was isolated, washed with approximately 5 ml of acetonitrile and then dried under vacuum at ambient temperature for 24 hours.

Figure 3B:
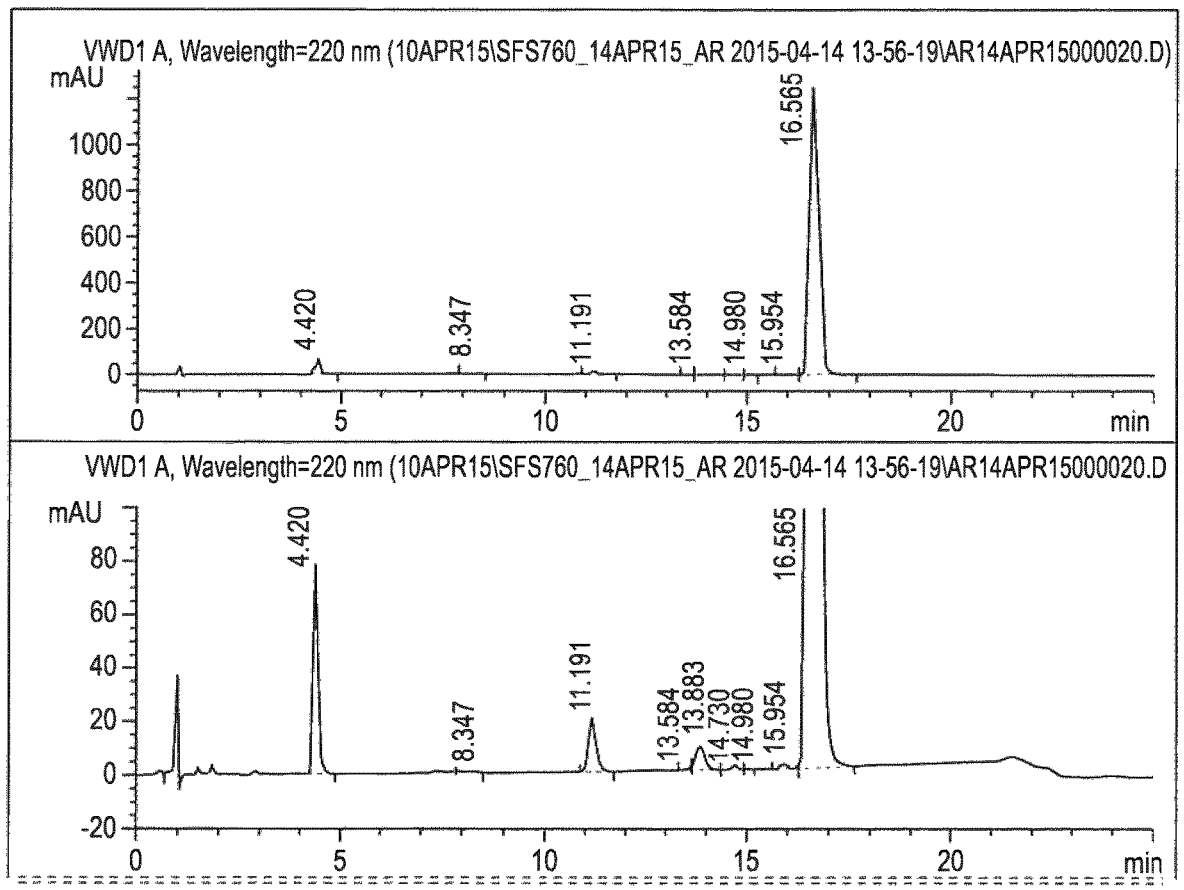

The next day the solids were analysed by HPLC for purity and assay (FIG. 3b), TG/DTA for ease of mass loss/thermal events (FIG. 4b) as well as polarised light microscopy (PLM) and XRPD for morphology and crystalline content.

The PLM analysis indicated that the final isolated solid comprised a mixture of agglomerates (50-100 μm), that easily dispersed to very small needle-like crystals (length<10 μm).

Figure 4B:
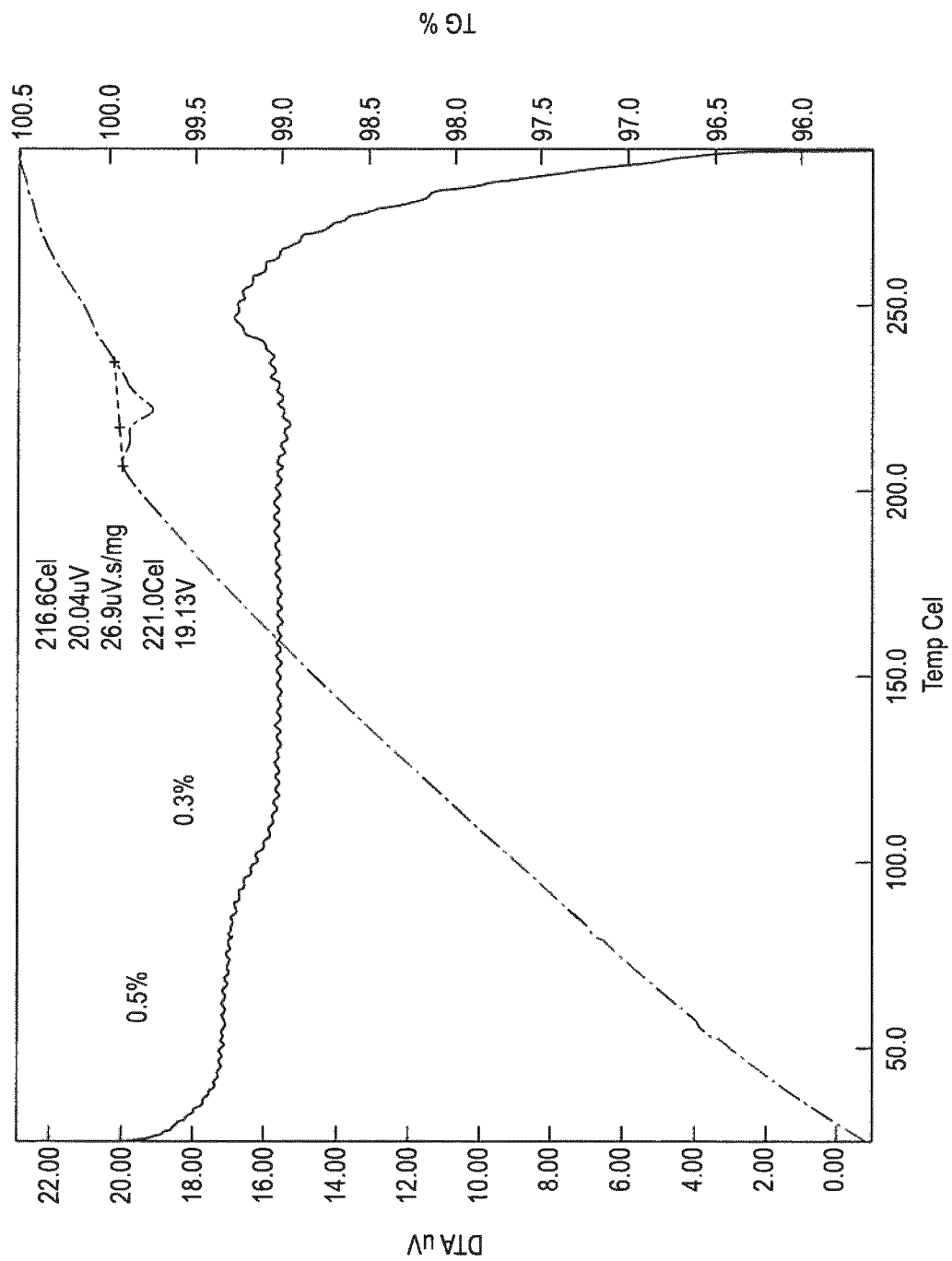

The TG/DTA data for crystals formed by the Example 4 method and shown in FIG. 4b shows that there was a total mass loss of only approximately 0.8% up to 110° C. This was found to be a two-step process, with a first mass loss of approximately 0.5% up to approximately 60° C., and a second mass loss of approximately 0.3% up to approximately 110° C. These mass losses correspond to weakly surface bound acetonitrile and water, and are not indicative of any solvation of the crystal form itself. Accordingly, the loss of this solvent does not alter the crystallinity of the desolvated crystalline Form II.

These results indicate that the desolvated crystalline Form II carbetocin is highly stable.

Example 5—Preparation of Solvated Crystalline Form I Carbetocin

Step i: Synthesis

Crude carbetocin of purity approx. 93.5% was obtained by synthetic methods analogous to those described in WO2009/122285 (International Patent Application No. PCT/IB2009/005351) of Ferring B.V.

Step ii: Preparation of the Solution

An acetate buffer, 25 mM, pH 5.5 was prepared from sodium acetate trihydrate, glacial acetic acid and ultrapure water. 354 mg crude carbetocin obtained in step i) was dissolved in 16.6 mL of the acetate buffer. The solution was filtered with a 0.22 μM PVDF syringe filter and 500 μL portions of the solution was aliquoted into vials which were thereafter sealed. The pH of the carbetocin solution was 5.3.

Step iii: Crystallisation

The solution obtained in step ii) was heated to 40° C. and kept in sealed vials at this temperature. After 3 days the vials were taken out and an Eppendorf glass pipette was used to gently suck the solution up and back in the vials to thereby create some seeds for the crystallisation. After the pipetting the vials were sealed again and maintained at 40° C. After 9 days particles with a crystal-like appearance had formed. The precipitated material was isolated.

XRPD analysis was carried out on a PANalytical X'pert pro with a Cu—K$\alpha_1$ monochromator ($\alpha_1$ λ=1.54060 Å). The samples were scanned between 2 and 35° 2θ. The material was gently crushed and smeared on a zero-background wafer of Si, which was then placed into a slow spinning sample holder in the diffractometer running in transmission mode (scan speed 0.01°/s, step size 0.017° 2θ) using 45 kV/40 mA generator settings. The measurements were performed using a programmable incident divergency slit.

The X-ray diffraction pattern of the carbetocin crystals obtained is presented in Table 3 and FIG. 5. The X-ray diffraction pattern indicates carbetocin with a different crystal form or polymorph when compared to Examples 1 and 2 (FIG. 1, Table 1) and Example 3 and 4 (FIG. 2, Table 2).

Differential scanning calorimetry (DSC) analysis was performed on a Netzsch DSC 204F1. Several milligrams of crystals were isolated from the mother solution and left to air dry in a fume hood for a few hours at about 20% relative humidity (RH). The crystals were gently crushed into a powder material and 1.2 mg of this material was charged into a 25 μL Al pan. A lid was adapted and crimped onto the pan, prior to being pierced with a pinhole (diameter 0.25 mm). The sample was analysed from 20 to 250° C. using a heating rate of 5 K/min.

Figure 7:
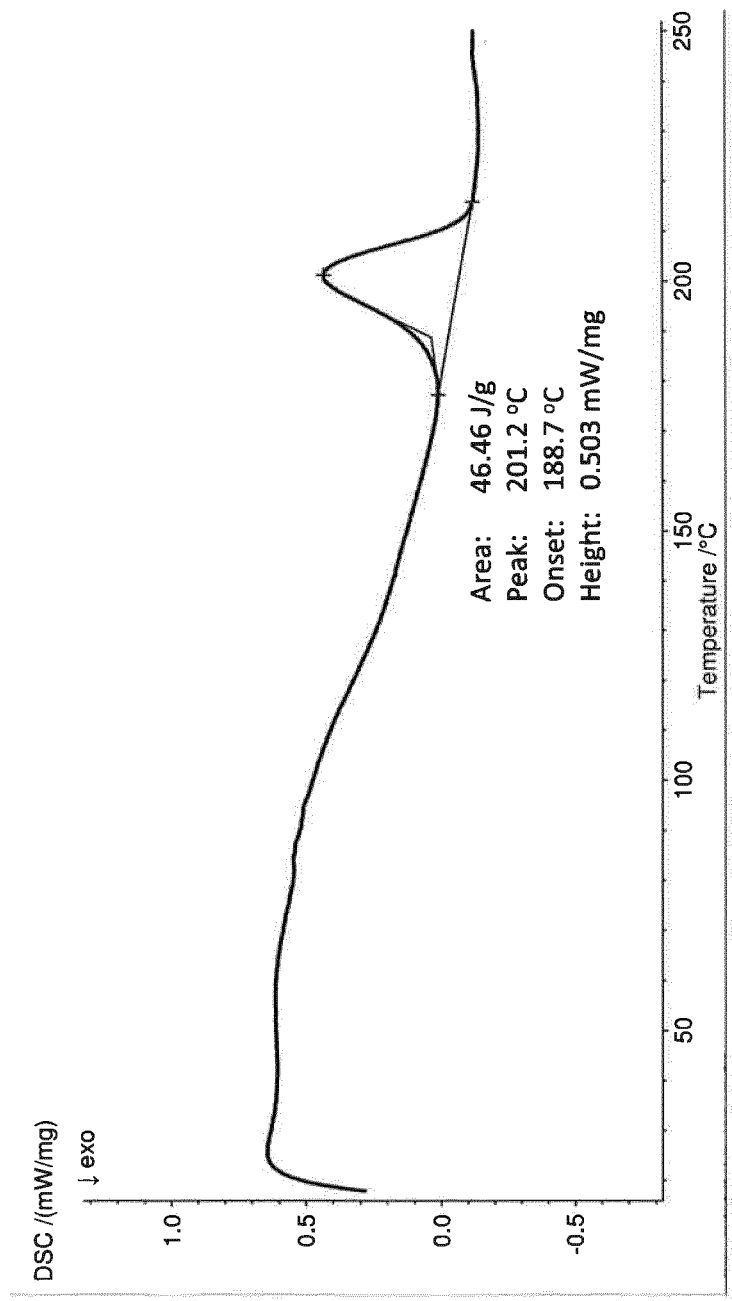
FIG. 7 shows differential scanning calorimetry (DSC) data relating to crystalline carbetocin isolated from Example 5.

The DSC data for crystals formed by the Example 5 method and shown in FIG. 7 shows that there is a loss of volatile material in the region of 40 to 120° C., corresponding to a loss of weakly surface bound water and solvated water. A melting endotherm with onset of 192° C. corresponds to the melting of anhydrous carbetocin.

Gravimetric vapour sorption (GVS) was performed on an SMS DVS-1. 1.4 mg of crystals and powder were added into an Al pan and exposed to stepwise relative humidity (RH) changes during two consecutive cycles: 20-30-40-50-60-70-80-70-60-50-40-30-20-10-0-10-20-30-40-50-60-70-80-90-80-70-60-50-40-30-20-10-0% RH in an open loop mode. The temperature was maintained at 25° C. and pure nitrogen flow rate of 200 ml/min was used. The dm/dt criteria applied was 0.001 weight-%/min during a 5 minute window, with a maximum time of 150 minutes for all steps, with the exception of steps at 0% RH that were set to 6 hours.

Figure 8A:
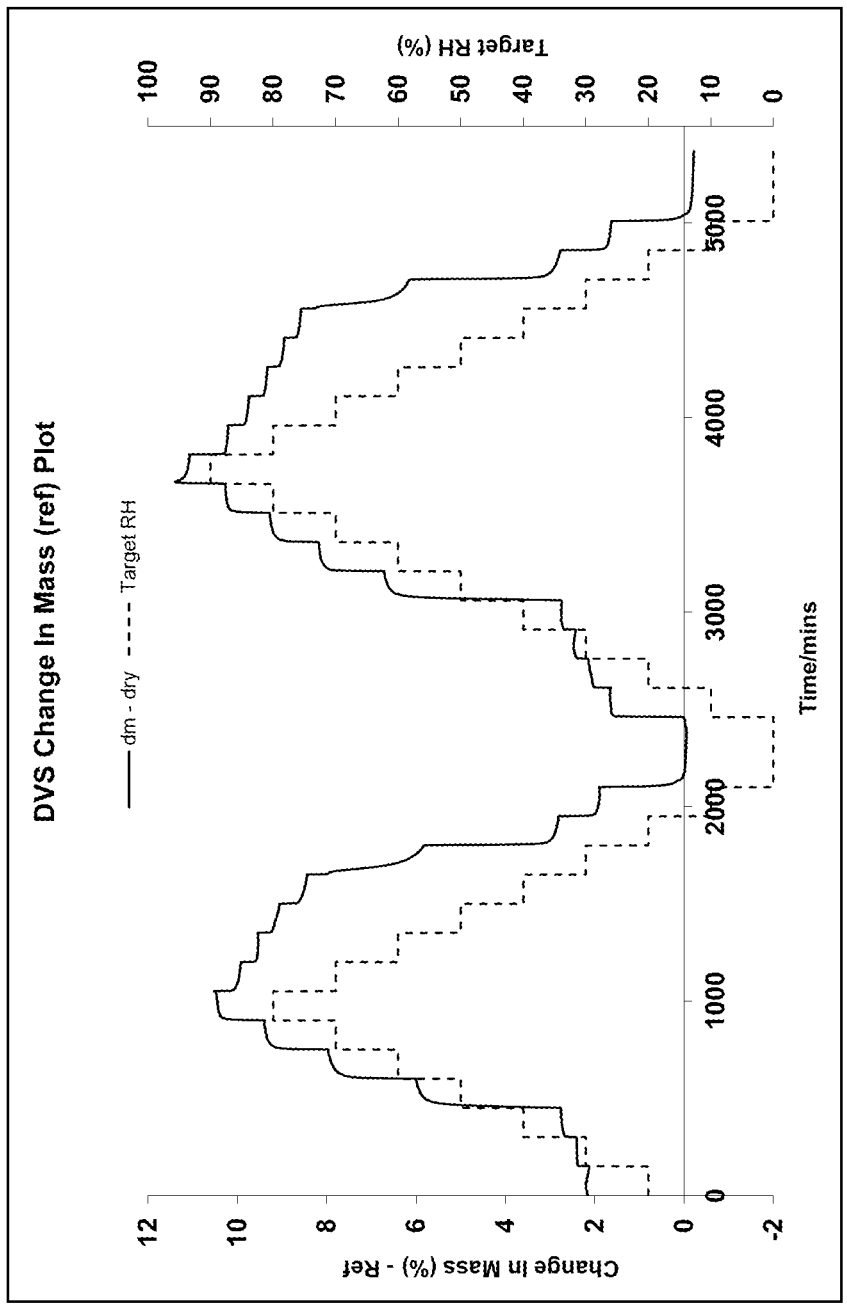
FIG. 8 shows gravimetric water sorption (GVS) data from crystalline carbetocin isolated from Example 5: change in mass plot (FIG. 8a) and isotherm plot (FIG. 8b).
Figure 8B:
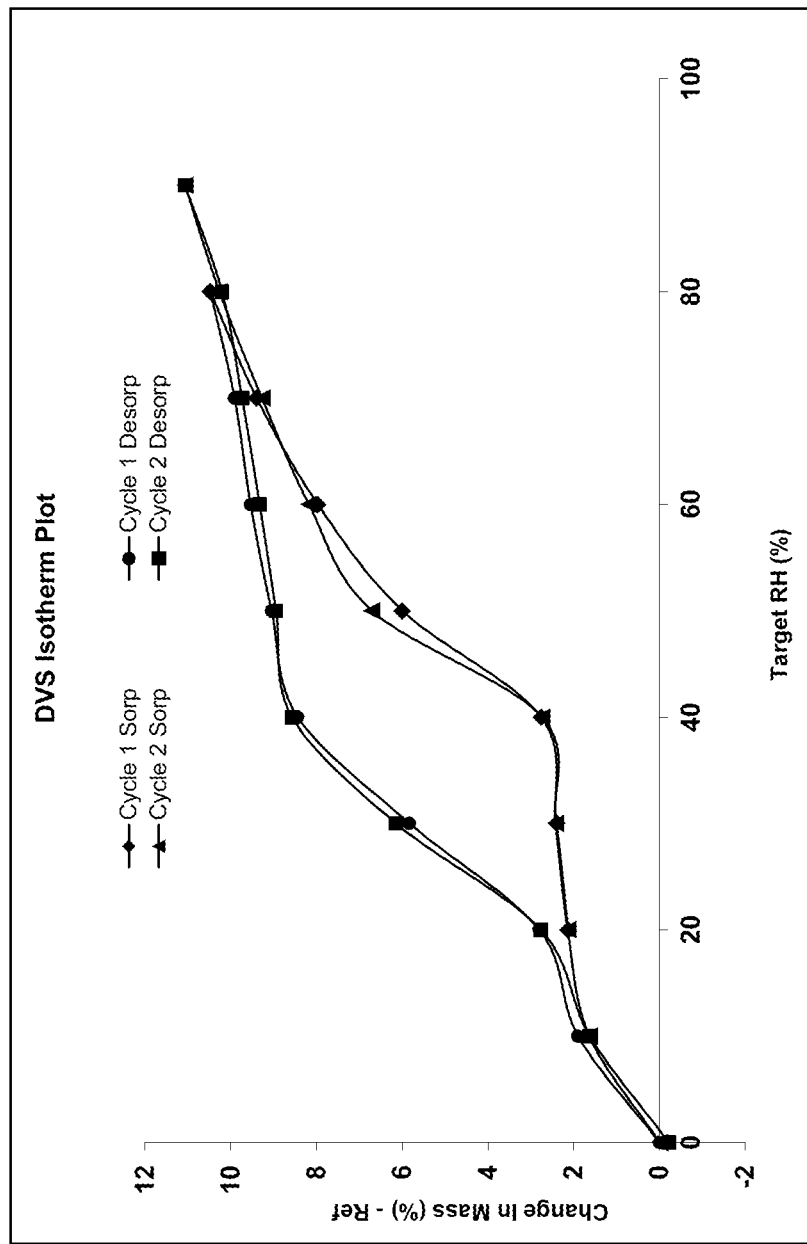

The GVS data are shown in FIG. 8. A GVS isotherm plot is shown in FIG. 8b. A plateau at around 2% (w/w) corresponds to a monohydrate plus some loosely bound surface water. A second plateau at an additional approximately 8% (w/w) corresponds to a pentahydrate with some loosely bound surface water. The pentahydrate exists at about 60% RH and above (sorption) and from about 40 to 90% RH (desorption).

The purity of the carbetocin in the (solvated) crystalline form was calculated at 98.7% by UV-HPLC according to the method outlined in Table 6.

TABLE 6

Analytical HPLC parameters for Example 5

| Parameter | Setting |
|---|---|
| LC | HPLC including: |
| | Gradient pump |
| | UV detector |
| | Autosampler |
| | Column heater (60° C.) |
| Column | Waters XBridge C18, 150 × 2.1 mm, 3.5 μm |
| Mobile phase A | ammonium acetate 0.15 g/L in 19% MeCN (acetonitrile) in water |
| Mobile phase B | ammonium acetate 0.075 g/L in ~60% MeCN (acetonitrile) in water |
| Flow rate | 0.4 mL/min. |
| Injection volume | 20 μL |
| Detection | UV 220 nm |
| Column temperature | 60° C. |
| Autosampler temperature | 5° C. |

| Gradient | Time (min.) | % A | % B |
|---|---|---|---|
| | 0 | 100 | 0 |
| | 20 | 75 | 25 |
| | 30 | 0 | 100 |
| | 31 | 100 | 0 |
| | 40 | 100 | 0 |
| Sample preparation | Crystals dissolved in milli-Q water and diluted to approx. 0.1 mg/mL with milli-Q water | | |
| Evaluation of results | Purity determined as relative UV area % of total area. | | |

What is claimed is:

1. Carbetocin in a crystalline form selected from solvated crystalline Form I and desolvated crystalline Form II.

2. The carbetocin according to claim 1, wherein the carbetocin is in solvated crystalline Form I.

3. The carbetocin according to claim 1, wherein the carbetocin is in desolvated crystalline Form II.

4. The carbetocin according to claim 2, characterised by X-ray powder diffraction peaks at about 4.83, 7.43, 9.20, 17.87, 19.60, 20.43 and 21.34 degrees 2θ (Cu—K).

5. The carbetocin according to claim 2, characterised by an X-ray powder diffraction pattern substantially as illustrated in FIG. 1.

6. The carbetocin according to claim 3, characterised by X-ray powder diffraction peaks at about 4.11, 4.39, 5.60, 7.45, 17.75, 19.16 and 19.45 degrees 2θ (Cu—K).

7. The carbetocin according to claim 3, characterised by an X-ray powder diffraction pattern substantially as illustrated in FIG. 2.

8. A pharmaceutical composition comprising the carbetocin according to claim 1.

9. A method of manufacturing a carbetocin in crystalline form according to claim 1, wherein the carbetocin in crystalline form is crystallised from a mixture comprising carbetocin and one or more liquid(s), the one or more liquid(s) comprising ethylene glycol and acetonitrile in a ratio of from 1:99 to 50:50 (v/v).

10. A method according to claim 9, wherein the carbetocin in crystalline form is obtained by cooling the mixture comprising carbetocin and one or more liquid(s) or by cycling the temperature of the mixture comprising carbetocin and one or more liquid(s).

11. A method according to claim 9, further comprising adding an antisolvent to the mixture comprising carbetocin and one or more liquid(s).

12. A method according to claim 11 wherein the one or more liquid(s) comprises a mixture of ethylene glycol and acetonitrile and the antisolvent comprises acetonitrile.

13. A method according to claim 12, wherein the one or more liquid(s) comprises ethylene glycol and acetonitrile in a ratio of from 15:85 to 25:75 (v/v), and wherein the addition of the acetonitrile antisolvent alters the ratio of ethylene glycol to acetonitrile to a ratio of from 1:99 to 30:70 (v/v).

14. A method according to claim 9, further comprising seeding the mixture comprising carbetocin and one or more liquid(s) with a crystal.

15. A method according to claim 9, further comprising desolvating and, optionally, drying, the carbetocin in crystalline form.

16. A method according to claim 15, wherein the method comprises desolvating the carbetocin in crystalline form by washing the carbetocin in crystalline form in an antisolvent, optionally at a temperature at or below 20° C.

17. A method of treatment of a neurological disorder or reproductive disorder comprising administering the pharmaceutical composition of claim 8 to a subject in need thereof.

18. The method of claim 17, wherein the neurological disorder or reproductive disorder is selected from one or more of Prader-Willi syndrome, uterine atony, and excessive bleeding following vaginal delivery.

19. Carbetocin in a crystalline form characterised by X-ray powder diffraction peaks at about 4.34, 6.43, 8.66, 17.37, 19.03, and 19.39 degrees 2θ (Cu—Kα$_1$).

20. The carbetocin according to claim 19, characterised by an X-ray powder diffraction pattern substantially as illustrated in FIG. 5.

21. A pharmaceutical composition comprising the carbetocin according to claim 19.

22. A method of manufacturing carbetocin in crystalline form according according to claim 19, wherein the carbetocin in crystalline form is crystallised from a mixture comprising carbetocin and one or more liquid(s), the one or more liquid(s) comprising one or both of water and aqueous acetate buffer.

23. A method according to claim 22, wherein the carbetocin in crystalline form is obtained by maintaining the mixture comprising carbetocin and one or more liquid(s) at a temperature of at least 15° C. for 3 to 100 days to crystallise carbetocin.

24. A method of treatment of a neurological disorder or reproductive disorder comprising administering the pharmaceutical composition of claim 21 to a subject in need thereof.

25. The method of claim 24, wherein the neurological disorder or reproductive disorder is selected from one or more of Prader-Willi syndrome, uterine atony, and excessive bleeding following vaginal delivery.

* * * * *

UNITED STATES PATENT AND TRADEMARK OFFICE
CERTIFICATE OF CORRECTION

| | |
|---|---|
| PATENT NO. | : 10,981,955 B2 |
| APPLICATION NO. | : 16/637499 |
| DATED | : April 20, 2021 |
| INVENTOR(S) | : Elizabeth Serrano Chavez et al. |

It is certified that error appears in the above-identified patent and that said Letters Patent is hereby corrected as shown below:

On the Title Page

Item (72), please correct the spelling of the last name of inventor:
"Helen Sjoergren"
To read:
Helen Sjoegren

Signed and Sealed this
Twenty-eighth Day of March, 2023

*Katherine Kelly Vidal*

Katherine Kelly Vidal
*Director of the United States Patent and Trademark Office*